United States Patent [19]

Fauran et al.

[11] 4,179,519

[45] Dec. 18, 1979

[54] METHOD AND COMPOSITION FOR REDUCING SERUM LIPID LEVELS USING P-CHLOROPHENYL P-CHLOROPHENOXYISOBUTYRATE

[75] Inventors: François Fauran, Castanet Tolosan; Clause Feniou, Pessac; Jacquelin Mosser, St. Medard en Jalles; Gisële Prat, Talence, all of France

[73] Assignee: Laboratoires Sarget, Merignac, France

[21] Appl. No.: 884,497

[22] Filed: Mar. 8, 1978

[51] Int. Cl.² .................................. A61K 31/235
[52] U.S. Cl. ................................... 424/308
[58] Field of Search ........................ 424/308

[56] References Cited

PUBLICATIONS

Farmhispania–Chem. Abst., vol. 82 (1975), p. 31145y.
Howard–Chem. Abst., vol. 77 (1972), p. 43438f.

*Primary Examiner*—Sam Rosen
*Attorney, Agent, or Firm*—Oblon, Fisher, Spivak, McClelland & Maier

[57] ABSTRACT

A method for reducing serum lipid levels in humans and animals is provided which comprises administering a hypolipidemically effective amount of p-chlorophenyl 2-(p-chlorophenoxy)-2-methylpropionate. A hypolipidemic composition is provided which comprises p-chlorophenyl 2-(p-chlorophenoxy)-2-methylpropionate, as principal active ingredient, in combination with a pharmaceutically acceptable carrier. Total serum lipids and serum cholesterol levels are significantly reduced.

7 Claims, No Drawings

METHOD AND COMPOSITION FOR REDUCING SERUM LIPID LEVELS USING P-CHLOROPHENYL P-CHLOROPHENOXYISOBUTYRATE

BACKGROUND OF THE INVENTION

1. Field of the Invention

The present invention relates to therapeutic applications in humans and animals of the p-chlorophenyl ester of p-chlorophenoxyisobutyric acid.

2. Description of the Prior Art

A number of esters and salts of clofibric acid and, in particular, the ethyl ester (clofibrate), the 3-dimethylcarbamoylpropyl ester (clofibride), and the aluminum, calcium and pyridoxine salts are used in therapy. We have now discovered that the p-chlorophenyl ester shows a very low toxicity and a hypolipidemic activity superior to that of clofibric acid and nicotinic acid.

The p-chlorophenyl ester of clofibric acid is a known chemical product (M. Julia et al, *Bull. Soc. Chim. France*, 1956, 776–83). Nevertheless, the therapeutic applications of this product have never before been described.

Both clofibric acid and nicotinic acid have been used as hypolipidemic agents, however a need continues to exist for hypolipidemic agents having even lower toxicity and higher activity than the above.

SUMMARY OF THE INVENTION

Accordingly, one object of the invention is to provide a hypolipidemic composition of low toxicity.

Another object of the invention is to provide a method of lowering serum lipid levels.

Briefly, these objects and other objects of the invention as hereinafter will become more readily apparent can be attained by providing a hypolipidemic composition which comprises p-chlorophenyl 2-(p-chlorophenoxy)-2-methylpropionate, as principal active ingredient, in combination with a pharmaceutically acceptable carrier; and a method of reducing serum lipid levels in humans or animals which comprises administering a hypolipidemically effective amount of p-chlorophenyl 2-(p-chlorophenoxy)-2-methylpropionate.

DETAILED DESCRIPTION OF THE PREFERRED EMBODIMENTS

The present inventors have now discovered that the p-chlorophenyl ester of clofibric acid shows a very low toxicity and a hypolipidemic activity significantly superior to that of both clofibric acid and nicotinic acid for reducing both total serum lipid levels and serum cholesterol levels.

The preparation of this ester may be performed according to classical methods. One example of this preparation is the following.

EXAMPLE

A mixture of 43 gm of p-chlorophenoxyisobutyric acid, 200 cc of benzene, and 40 cc of $SOCl_2$ is heated at reflux for 2 hours. The benzene and the thionyl chloride are evaporated until the temperature reaches 80° C. The resulting acid chloride of clofibric acid is vacuum distilled. $B.p._{0.4\ mm} = 112°$ C.

To a mixture of 300 cc of benzene, 30 gm of triethylamine, and 26 gm of p-chlorophenol is added dropwise 40 gm of the acid chloride of clofibric acid. The temperature of the reaction mixture rises. The reaction mixture is stirred for 6 hours. The triethylamine hydrochloride is separated by filtration. The benzene phase is washed with cold dilute sodium hydroxide, and then washed with water. The benzene phase is dried and then evaporated. The residue is vacuum distilled to yield 43 gm of the ester, $b.p._{0.2\ mm} = 165°$ C. The liquid so obtained is poured into a mortar. Crystallization is induced with a glass rod. The ester crystallizes in the form of a white solid, melting at 48° C.

The NMR spectrum is $CDCl_3$ (internal reference, TMS) shows a singlet centered at 1.7 ppm corresponding to the 6 methyl protons and a complex multiplet at 6.7–7.4 ppm corresponding to 8 aromatic protons.

PHARMACOLOGICAL STUDY

The acute toxicity of the p-chlorophenyl ester of clofibric acid was determined using two species of animals (Swiss EOPS mice and Wistar EOPS rats) by oral administration, the product being administered in a gum preparation. The animals were observed during 14 days. For the mice, a dose of 2000 mg/kg resulted in 10% mortality. For the rat, a dose of 2000 mg/kg did not result in any mortality, whereas the same dose of clofibric acid resulted in 40% mortality.

The hypolipidemic activity was determined in rats subjected to a regimen rich in lipids over the course of 2 sets of experiments.

1. Conventional male Wistar rats weighing 130–150 g were maintained on a regimen rich in lipids for 21 days. At the same time, beginning with the fifteenth day of the regimen, they received a daily dose of either a gum preparation containing the product to be tested or a preparation of 6% gum arabic alone. After a fast of 24 hours, the animals were sacrificed, 22 days after the start of the regimen. The results are presented in Table I. The percentage reductions of the lipid levels were calculated using the following equation:

$$\% \text{ reduction} = \frac{\text{levels for hyperlipidemic rats} - \text{levels for treated rats}}{\text{levels for hyperlipidemic rats} - \text{levels for normal rats}} \times 100$$

The reductions in blood and liver levels are significant only in the case of the p-chlorophenyl ester of clofibric acid.

2. Male Wistar EOPS rats weighing in the neighborhood of 140 g receive a regimen rich in lipids during 21 days. Beginning with the eleventh day, the animals receive either a gum preparation containing the product to be tested or a preparation of 6% gum arabic alone, for 6 days out of 7. After the last feeding, and a subsequent 24 hour fast, the animals are sacrificed. A group of animals submitted to a normal regimen is used as a control. The results are present in Table II. The percentage reductions of lipid levels are calculated using the following equation:

$$\% \text{ reduction} = \frac{\text{levels for hyperlipidemic rats} - \text{levels for treated rats}}{\text{levels for hyperlipidemic rats} - \text{levels for normal rats}} \times 100$$

TABLE I

| TREATMENT | SERUM | | | | LIVER | |
|---|---|---|---|---|---|---|
| | TOTAL LIPIDS | | CHOLESTEROL | | TOTAL LIPIDS | |
| | concentration in g/l | % reduction | concentration in g/l | % reduction | level in mg/g of liver | % reduction |
| Normal regimen | 3.53 ± 1.16 | | 0.85 ± 0.10 | | 33.15 ± 12.54 | |
| Regimen rich in lipids | 5.32 ± 1.43 | | 2.41 ± 0.86 | | 96.27 ± 19.26 | |
| Regimen + nicotinic acid 200 mg/kg/day 1.626 mmole/kg/day | 6.38 ± 1.55 | | 2.33 ± 0.67 | 5 | 91.62 ± 19.94 | 7 |
| Regimen + p-chlorophenyl ester of clofibric acid 200 mg/kg/day 0.615 mmole/kg/day | 3.87 ± 0.65 | 81 | 1.33 ± 0.33 | 69 | 60.82 ± 26.98 | 56 |

TABLE II

| TREATMENT | SERUM | | | | | LIVER | | | | Wt. of liver Wt of rat |
|---|---|---|---|---|---|---|---|---|---|---|
| | Total lipids | | Cholesterol | | Triglycerides concentration in g/l | Total Lipids | Cholesterol level in mg/g of liver | Triglycerides | | |
| | concentration in g/l | % reduction | concentration in g/l | % reduction | | | | level in mg/g of liver | % reduction | |
| Normal regimen | 2.24 ± 0.48 | | 0.70 ± 0.08 | | 0.55 ± 0.12 | 22.2 ± 5.9 | 4.4 ± 0.9 | 14.20 ± 4.62 | | 2.90 ± 0.23 |
| Regimen rich in lipids | 7.26 ± 2.54 | | 4.17 ± 1.58 | | 0.63 ± 0.16 | 285.2 ± 52.5 | 121.6 ± 8.0 | 31.74 ± 4.58 | | 5.71 ± 0.39 |
| Regimen + p-chlorophenyl ester 75 mg/kg/day 0,231 mmole/kg/day | 5.56 ± 2.83 NS | 34 | 3.06 ± 1.67 NS | 32 | 0.39 ± 0.06 S | 323.9 ± 100.7 | 123.0 ± 20.2 | 23.37 ± 4.57 S | 48 | 6.08 ± 0.31 |
| Regimen + p-chlorophenyl ester 125 mg/kg/day 0,384 mmole/kg/day | 3.55 ± 0.77 S | 74 | 1.79 ± 0.48 S | 69 | 0.35 ± 0.06 S | 361.9 ± 71.1 | 136.5 ± 14.3 | 20.84 ± 4.46 S | 62 | 6.36 ± 0.31 |
| Regimen + p-chlorophenyl ester 200 mg/kg/day 0,615 mmole/kg/day | 3.81 ± 0.97 S | 69 | 1.84 ± 0.44 S | 67 | 0.22 ± 0.06 S | 382.0 ± 54.6 | 135.2 ± 21.8 | 16.20 ± 2.27 S | 89 | 6.70 ± 0.50 |
| Regimen + clofibric acid 125 mg/kg/day 0,515 mmole/kg/day | 4.97 ± 1.41 S | 46 | 2.31 ± 0.68 S | 54 | 0.23 ± 0.04 S | 382.7 ± 43.5 | 127.0 ± 18.4 | 20.33 ± 2.68 S | 65 | 6.99 ± 0.75 |

The notations NS or S indicate the significance of the results obtained in the treated groups compared to the groups submitted only to a regimen rich in lipids.

At equal dosage levels, the p-chlorophenyl ester reduces serum lipid and cholesterol levels to a greater degree than the acid. These differences are significant. The weight of the animals' livers increases using the p-chorophenyl ester but at equivalent dosage levels, the increase in weight is smaller than when the acid is used, and this difference is statistically significant.

A subchronic toxicity study of the p-chlorophenyl ester of clofibric acid was carried out using the following protocol. The product was administered six days a week during the course of a month, by oral administration in a gum preparation, to male Wistar EOPS rats having an average initial weight of 200 g. After the last feeding, the animals were fasted. A blood sample is taken from the abdominal aorta under anesthesia, then the animals are sacrificed. Table III shows the results of sampling the blood levels. The notation NS or S signifies whether the change induced by the product to be tested was statistically nonsignificant or significant.

In view of its pharmacological activity and its low toxicity, the p-chlorophenyl ester of p-chlorophenoxyisobutyric acid is therapeutically useful for treatment of lipid disfunction (hypercholesterolemia with or without xanthomatosis, hypertriglyceridemia, combined hyperlipidemia) as well as atherosclerotic conditions such as coronary insufficiency, cerebral vascular conditions, arteritis of inferior members, and arterial hypertension.

TABLE III

| TREATMENT | UREA g/l | GLYCEMIA g/l | ALKALINE PHOSPHATASE mU/ml | BILIRUBIN g/l | TOTAL LIPIDS g/l | CHOLESTEROL g/l | TRIGLYCERIDES g/l |
|---|---|---|---|---|---|---|---|
| Gum arabic 6% | 0.46 ± 0.10 | 1.42 ± 0.26 | 29.9 ± 6.6 | 4.14 ± 1.24 | 3.82 ± 0.63 | 0.63 ± 0.11 | 0.90 ± 0.16 |
| p-Chlorophenyl ester 100 mg/kg/day | 0.42 ± 0.07 NS | 1.58 ± 0.15 NS | 25.0 ± 4.9 NS | 3.68 ± 0.73 NS | 2.92 ± 0.54 S | 0.47 ± 0.04 S | 0.83 ± 0.27 NS |
| p-Chlorophenyl ester | 0.34 ± 0.07 S | 1.57 ± 0.15 NS | 33.5 ± 7.8 NS | 4.82 ± 1.85 NS | 2.54 ± 0.35 S | 0.37 ± 0.07 S | 0.74 ± 0.1 NS |
| p-Chlorophenyl ester 500 mg/kg/day | 0.40 ± 0.05 NS | 1.41 ± 0.26 NS | 38.4 ± 9.9 NS | 5.04 ± 1.09 NS | 2.77 ± 0.42 S | 0.32 ± 0.06 S | 1.09 ± 0.33 NS |

The active principle may be administered in association with appropriate vehicles and in various pharmaceutically acceptable forms, for example by oral administration in unit dosage form such as gels, capsules, tablets and lozenges at a dose of 0.1 to 2.5 g per day in 2 to 4 administrations per day.

What is claimed as new and intended to be covered by Letters Patent is:

1. A method of reducing serum lipid levels in humans or animals which comprises administering a hypolipidemically effective amount of p-chlorophenyl 2-(p-chlorophenoxy)-2-methylpropionate.

2. The method of claim 1, wherein said p-chlorophenyl 2-(p-chlorophenoxy)-2-methylpropionate is administered in combination with a pharmaceutically acceptable carrier.

3. The method of claim 1 wherein said hypolipidemically effective amount is from 0.1 to 2.5 grams per day, administered orally.

4. A hypolipidemic composition in unit dosage form, which comprises, per dosage unit, a hypolipidemically effective amount of p-chlorophenyl 2-(p-chlorophenoxy)-2-methylpropionate, as principal active ingredient, in combination with a pharmaceutically acceptable carrier.

5. The hypolipidemic composition of claim 4, in a form adapted for oral administration.

6. The hypolipidemic composition of claim 5, wherein said p-chlorophenyl 2-(p-chlorophenoxy)-2-methylpropionate is contained in each said dosage unit in a concentration such that from 2 to 4 administrations per day of said dosage units contains from 0.1 to 2.5 grams of said p-chlorophenyl 2-(p-chlorophenoxy)-2-methylpropionate.

7. The hypolipidemic composition of claim 5, in the form of gels, capsules, tablets or lozenges.

* * * * *

UNITED STATES PATENT AND TRADEMARK OFFICE
CERTIFICATE OF CORRECTION

PATENT NO. : 4,179,519
DATED : Dec. 18, 1979
INVENTOR(S) : FRANCOIS FAURAN ET AL

It is certified that error appears in the above-identified patent and that said Letters Patent are hereby corrected as shown below:

Please change the third inventor's name as follows:

[75] --Jacqueline Mosser--

Please insert the following Priority Data:

[30] --March 8, 1977 [FR]    France.....77 06689---

Signed and Sealed this

Twenty-sixth Day of August 1980

[SEAL]

Attest:

SIDNEY A. DIAMOND

Attesting Officer          Commissioner of Patents and Trademarks